(12) United States Patent
Masuda et al.

(10) Patent No.: US 7,905,881 B2
(45) Date of Patent: Mar. 15, 2011

(54) SURGICAL INSTRUMENT

(75) Inventors: Shinya Masuda, Hino (JP); Taro Miyazawa, Hino (JP); Kazunori Taniguchi, Hachioji (JP); Hiroshi Okabe, Hachioji (JP)

(73) Assignee: Olympus Medical Systems Corp. (JP)

( * ) Notice: Subject to any disclaimer, the term of this patent is extended or adjusted under 35 U.S.C. 154(b) by 669 days.

(21) Appl. No.: 11/459,411

(22) Filed: Jul. 24, 2006

(65) Prior Publication Data

US 2008/0132887 A1 Jun. 5, 2008

(30) Foreign Application Priority Data

Jul. 4, 2006 (JP) .................................. 2006-184663

(51) Int. Cl.
*A61B 18/18* (2006.01)
(52) U.S. Cl. .............................. 606/37; 606/51; 606/169
(58) Field of Classification Search .................... 606/45, 606/49–52, 37
See application file for complete search history.

(56) References Cited

U.S. PATENT DOCUMENTS

| | | | | |
|---|---|---|---|---|
| 6,056,735 | A * | 5/2000 | Okada et al. ..................... | 606/1 |
| 6,083,223 | A | 7/2000 | Baker .............................. | 606/52 |
| 6,113,598 | A | 9/2000 | Baker .............................. | 606/51 |
| 6,669,690 | B1 * | 12/2003 | Okada et al. ..................... | 606/40 |
| 7,270,664 | B2 * | 9/2007 | Johnson et al. .................. | 606/51 |
| 7,329,257 | B2 * | 2/2008 | Kanehira et al. ................ | 606/52 |
| 7,396,356 | B2 * | 7/2008 | Mollenauer ..................... | 606/51 |
| 2005/0159745 | A1 | 7/2005 | Truckai et al. .................. | 606/51 |
| 2006/0259054 | A1 * | 11/2006 | Masuda et al. ................. | 606/169 |
| 2007/0043297 | A1 | 2/2007 | Miyazawa ...................... | 600/471 |

FOREIGN PATENT DOCUMENTS

| | | |
|---|---|---|
| JP | 2003-79633 | 3/2003 |
| JP | 2004 129870 | 4/2004 |
| JP | 2004 216180 | 8/2004 |
| JP | 2005-238979 | 9/2005 |
| JP | 2005-278933 | 10/2005 |
| JP | 2006-75376 | 3/2006 |
| JP | 2007-50181 | 3/2007 |
| WO | WO 2005/122918 | 12/2005 |
| WO | WO 2005122918 A1 * | 12/2005 |

OTHER PUBLICATIONS

European Search Report in Application No. 07012598 dated Nov. 12, 2007. Untranslated Japanese Office Action issued on Apr. 8, 2008 in connection with corresponding Japanese application No. 2006-184663.
English translation of Japanese Office Action issued in connection with 2006-184663 submitted in lieu of statement of relevancy of prior art teachings to the instant application.
Concise explanation of relevance of Japanese patent application No. 2005-238979 to instant application prepared by applicant in lieu of English translation of reference.

* cited by examiner

*Primary Examiner* — Roy D Gibson
*Assistant Examiner* — Benjamin Lee
(74) *Attorney, Agent, or Firm* — Ostrolenk Faber LLP

(57) ABSTRACT

A surgical instrument has a first grasping member, a second grasping member which is provided to the first grasping member to open and close to the first grasping member, and grasps a living tissue between them, an ultrasonic coagulation-cutting unit which includes an ultrasonic vibrating portion provided in one of the first and second grasping members and connected to an ultrasonic transducer to generate ultrasonic vibration, and a pressing portion provided in the other of the first and second grasping members, and facing the ultrasonic vibrating portion, the pressing portion and the ultrasonic vibrating portion pressing the living tissue between them, and a high-frequency coagulation unit which includes a first electrode provided in the first grasping member, and a second electrode provided in the second grasping member, the first electrode and the second electrodes facing each other to coagulate the living tissue.

6 Claims, 11 Drawing Sheets

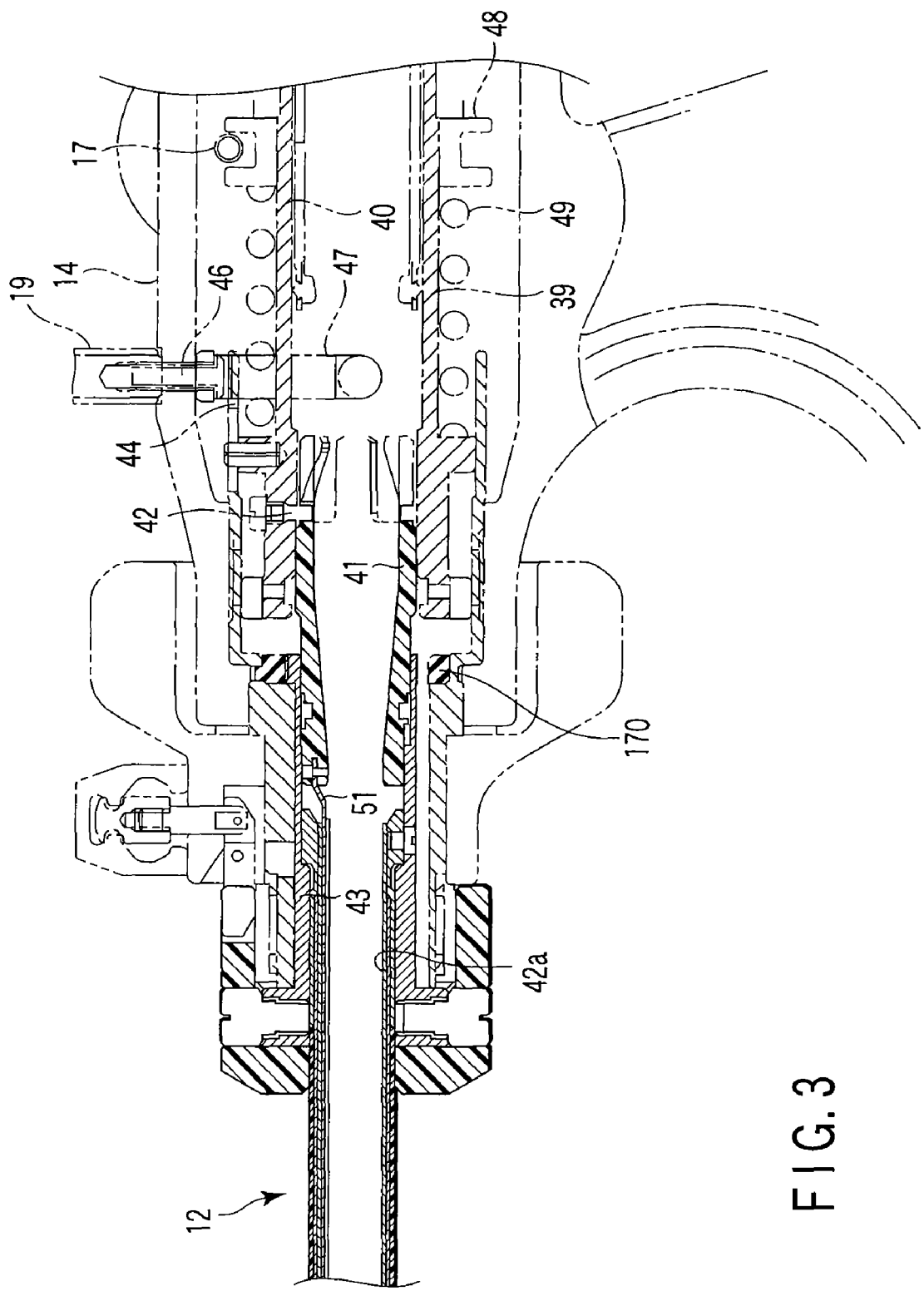
F I G. 3

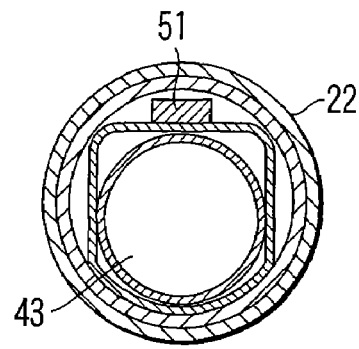
F I G. 6A
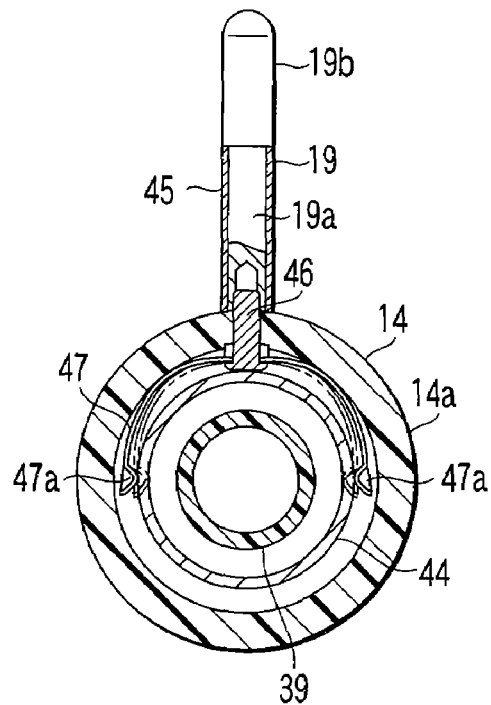
F I G. 4
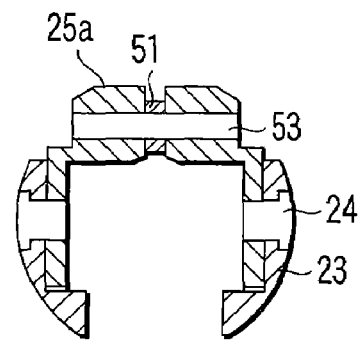
F I G. 6B
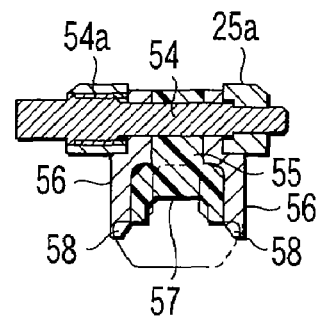
F I G. 6C

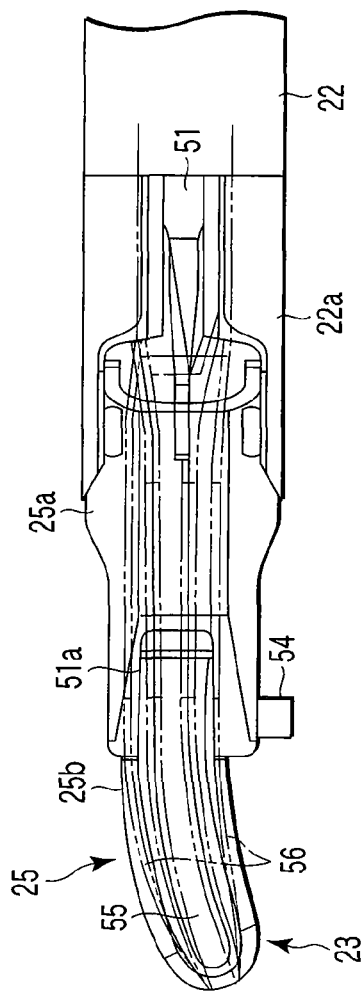
F I G. 5A
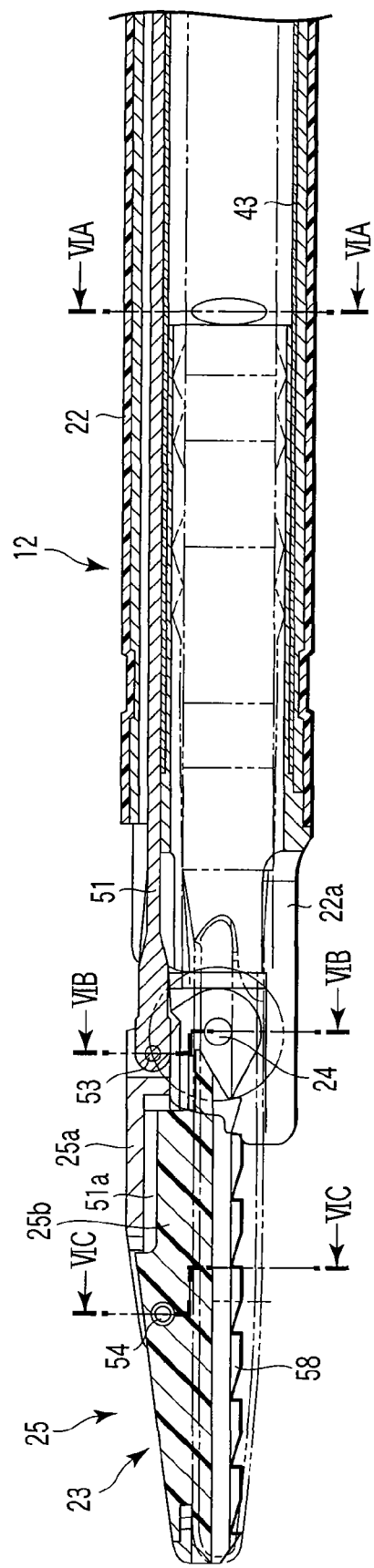
F I G. 5B

SURGICAL INSTRUMENT

CROSS-REFERENCE TO RELATED APPLICATIONS

This application is based upon and claims the benefit of priority from prior Japanese Patent Application No. 2006-184663, filed Jul. 4, 2006, the entire contents of which are incorporated herein by reference.

BACKGROUND OF THE INVENTION

1. Field of the Invention

The present invention relates to a surgical instrument, which grasps a living tissue, and coagulates and cuts the tissue by ultrasonic vibration and high-frequency current.

2. Description of the Related Art

Each of an ultrasonic instrument using ultrasonic vibration and a high-frequency instrument using a high-frequency current is known as a surgical instrument. An ultrasonic instrument can coagulate and cut a living tissue by heating the tissue with ultrasonic vibration. A high-frequency instrument can coagulate and cut a living tissue by touching an electrified electrode to the living tissue.

Surgical instruments which can treat a living tissue by using both ultrasonic vibration and high-frequency current are known by Jpn. Pat. Appln. KOKAI Publication Nos. 2003-79633, 2004-12987 and 2004-216180. In each of these surgical instruments, ultrasonic vibration generated by an ultrasonic transducer provided in an operation area is transmitted to a distal end portion of an ultrasonic probe through an ultrasonic vibration transmitting member, and a jaw is provided on the ultrasonic probe to be able to open and close to the probe. The jaw and the probe can grasp a living tissue between them. And, by supplying a high-frequency current from an externally provided high-frequency power supply to the ultrasonic probe, the tissue grasped between the ultrasonic probe and the jaw can be coagulated and cut by the high-frequency current.

The surgical instrument described in the Jpn. Pat. Appln. KOKAI Publication No. 2003-79633 has a round bar-shaped horn for generating ultrasonic vibration, and an open/close cover having an arc-shaped section and an electrode and provided on the horn to open and close thereto. A living tissue is grasped by the horn and cover, and coagulated and cut by the ultrasonic vibration from the horn and high-frequency current from the electrode of the cover. However, in this conventional surgical instrument, there is a problem that the living tissue cannot be grasped (compressed) by a strong force because the living tissue is grasped by the round bar-shaped horn and the arc-shaped sectioned open/close cover.

The surgical instrument described in each of the Jpn. Pat. Appln. KOKAI Publication Nos. 2004-129870 and 2004-216180 has a round bar-shaped horn for generating ultrasonic vibration, and a grasping member having an electrode and provided on the horn to open and close thereto. A living tissue is grasped by the horn and the grasping member, and coagulated and cut by the ultrasonic vibration from the horn and high-frequency current from the electrode of the grasping member. However, also in this conventional surgical instrument, there is a problem that the living tissue cannot be grasped (compressed) by a strong force because the living tissue is grasped by the round bar-shaped horn and the grasping member.

BRIEF SUMMARY OF THE INVENTION

A surgical instrument according to an aspect of the present invention, comprises: a first grasping member; a second grasping member which is provided to the first grasping member to open and close to the first grasping member, and grasps a living tissue between them; an ultrasonic coagulation-cutting unit which includes an ultrasonic vibrating portion provided in one of the first and second grasping members and connected to an ultrasonic transducer to generate ultrasonic vibration, and a pressing portion provided in the other of the first and second grasping members, and facing the ultrasonic vibrating portion, the pressing portion and the ultrasonic vibrating portion pressing the living tissue between them; and a high-frequency coagulation unit which includes a first electrode provided in the first grasping member, and a second electrode provided in the second grasping member, the first electrode and the second electrodes facing each other to coagulate the living tissue.

A surgical instrument according to another aspect of the present invention, comprises: a first grasping member; a second grasping member which is provided to the first grasping member to open and close to the first grasping member, and grasps a living tissue between them; an ultrasonic coagulation-cutting unit which includes an ultrasonic vibrating portion provided in one of the first and second grasping members and connected to an ultrasonic transducer to generate ultrasonic vibration, and a pressing portion provided in the other one of the first and second grasping members, facing the ultrasonic vibrating portion, the pressing portion and the ultrasonic vibrating portion pressing the living tissue between them; and a high-frequency coagulation unit which includes a first electrode provided in the first grasping member, and a second electrode provided in the second grasping member, and coagulates a living tissue, the first and second electrodes placed at positions to form a gap therebetween when the pressing portion and ultrasonic vibrating portion of the ultrasonic coagulation-cutting unit are put together by a grasping operation of the first and second grasping members.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is an enlarged sectional view of a distal end portion of the operation area of FIG. 2;

FIG. 4 is a transverse sectional view along a line of IV-IV in FIG. 2;

FIG. 5A is a plan view of a surgical treatment area of the surgical instrument of FIG. 1;

FIG. 5B is a longitudinal sectional view of the surgical treatment area of FIG. 5A;

FIG. 6A is a transverse sectional view along a line of VIA-VIA in FIG. 5B;

FIG. 6B is a transverse sectional view along a line of VIB-VIB in FIG. 5B;

FIG. 6C is a transverse sectional view along a line of VIC-VIC in FIG. 5B;

DETAILED DESCRIPTION OF THE INVENTION

First, a surgical instrument according to a first embodiment of the present invention will be explained with reference to FIG. 1 to FIG. 8.

Figure 1:
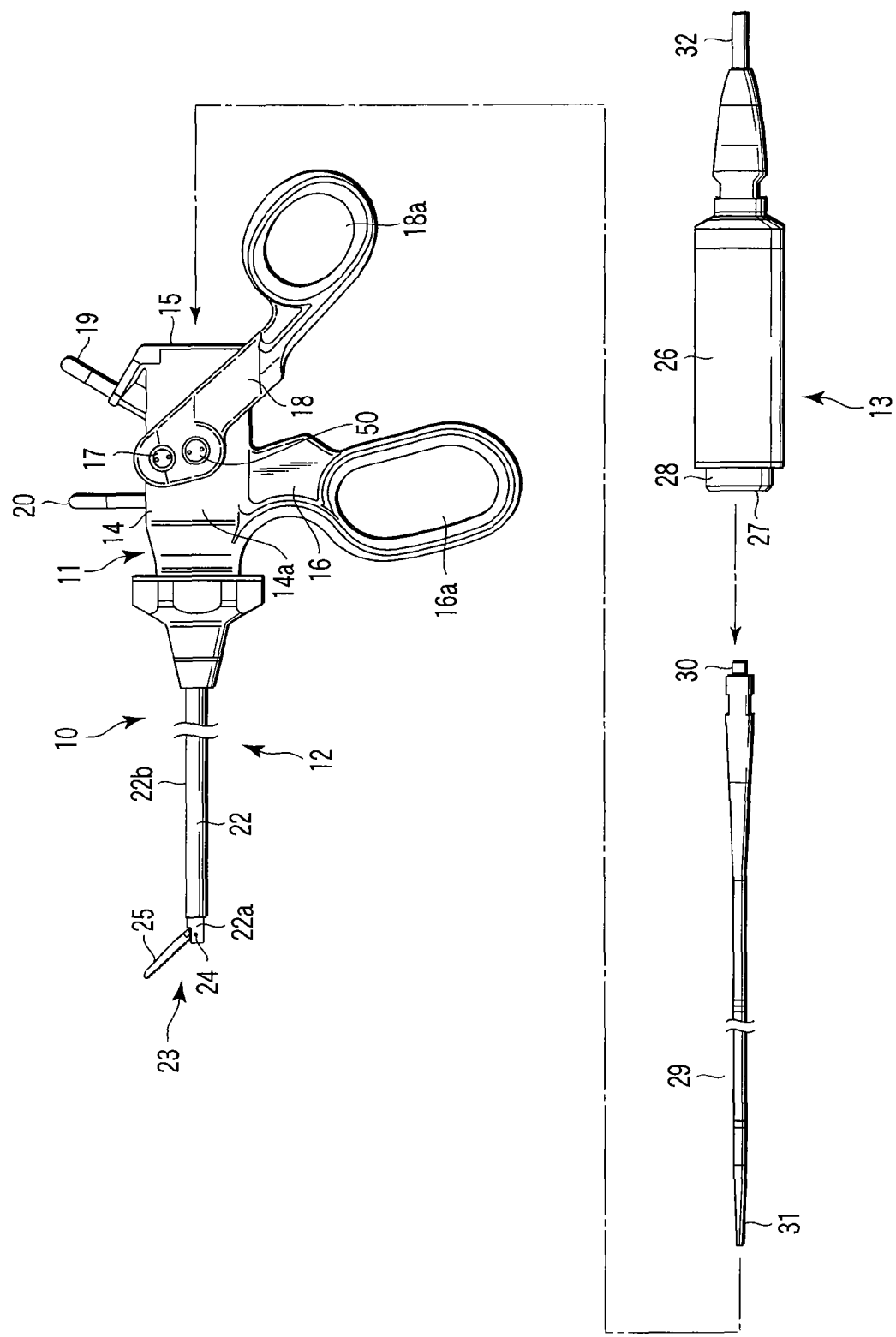
FIG. 1 is a side view schematically showing the whole of a surgical instrument according to a first embodiment of the invention.

As shown in FIG. 1, a surgical instrument 10 has an operation area 11, an insertion area 12 which is attachable to and detachable from the insertion area 11, a transducer unit 13 which is detachably inserted into the insertion area 12 from the proximal end portion of the operation area 11.

The operation area 11 has an operation area main body 14 having a cylindrical casing 14a. The proximal end portion of the operation area main body 14 is provided with a transducer unit connector 15 to which the transducer unit 13 is connected. A fixed handle 16 is integrally provided to the outer circumferential surface of the casing 14a of the operation area main body 14.

A movable handle 18 is provided to the casing 14a of the operation area main body 14 with a pivot 17. A finger insertion hole 16a is formed in the fixed handle 16, and fingers excepting the thumb of one hand of an operator can be selectively inserted into the finger insertion hole 16a. A thumb insertion hole 18a is formed in the movable handle 18, and the thumb of the same hand of the operator can be inserted into the thumb insertion hole 18a. The casing 14a of the operation area main body 14 is further provided with a first electrode pin 19 and a second electrode pin 20, both of which project from the body and can be connected to a high-frequency power supplying device (not shown).

An insertion sheath 22 of the insertion area 12 is detachably connected to the distal end portion of the casing 14a of the operation area main body 14. The insertion sheath 22 includes a tubular member which is made of electrically conductive material and the outer surface of which is covered by an insulating layer 22b, and a holding member 22a which is provided at the distal end portion of the tubular member. The holding member 22a holds a surgical treatment area 23. The surgical treatment area 23 includes a first grasping member 25 which is pivotally supported by a pivot pin 24 to be rotationally movable in a direction crossing the longitudinal center line of the insertion sheath 22.

The transducer unit 13 includes a transducer casing 26 which can be detachably connected to the transducer unit connecting part 15 of the operation area main body 14. A transducer for generating ultrasonic vibration is housed in the transducer casing 26. A unit connector 27 is provided at the distal end portion of the transducer casing 26. A C-shaped engaging ring 28 which is formed by cutting a part of a ring member is fit on the unit connector 27. The transducer unit 13 further includes a probe 29 as an ultrasonic vibration transmitting member. A fixing screw 30 which is detachably connected to the unit connector 27 is provided at the proximal end portion of the probe 29. The distal end portion of the probe 29 is configured as an ultrasonic vibrating portion 31. An electric cable 32 for generating ultrasonic vibration is extended from the proximal end of the transducer casing 26.

When the transducer casing 26 of the transducer unit 13 is fit into the transducer unit connector 15 of the operation area main body 14, the probe 29 of the transducer unit 13 is inserted into the tubular member of the insertion sheath 22, and the ultrasonic vibrating portion 31 at the distal end portion of the probe 29 is projected forward from the holding member 22a of the insertion sheath 22. The ultrasonic vibrating portion 31 at the distal end portion of the probe 29 projected forward from the holding member 22a of the insertion sheath 22 cooperates with the first grasping member 25 to form the surgical treatment area 23.

Figure 2:
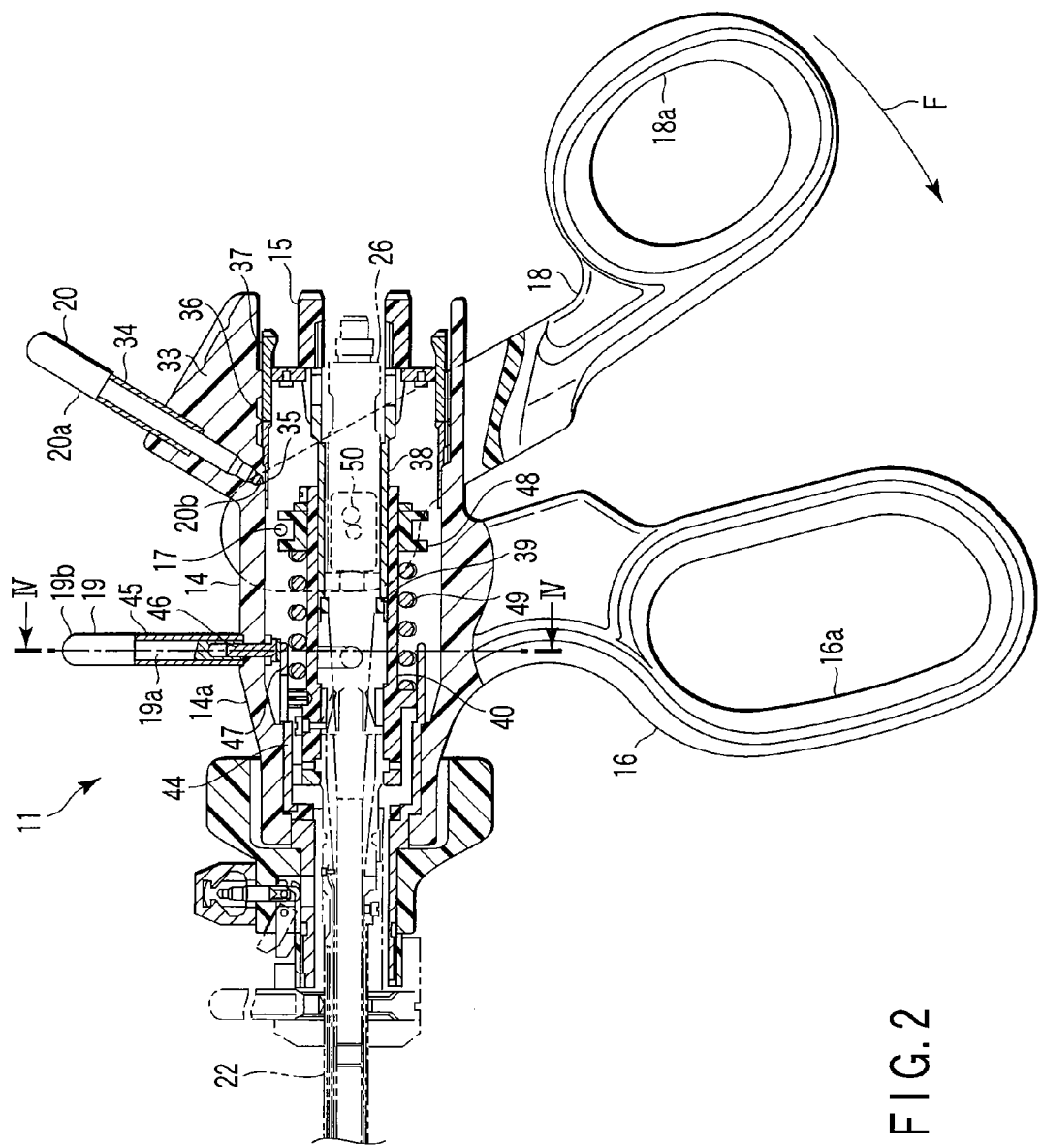
FIG. 2 is a longitudinal sectional view of an operation area of the surgical instrument of FIG. 1.

Next, the internal structure of the operation area 11 will be explained with reference to FIGS. 2 to 4. FIG. 2 is a longitudinal sectional view of the operation area 11 of the surgical instrument 10 of FIG. 1. FIG. 3 is an enlarged sectional view of the distal end portion of the operation area 11 of FIG. 2. And, FIG. 4 is a transverse sectional view along a line of IV-IV in FIG. 2.

As shown in FIG. 2, the casing 14a of the operation area main body 14 is made of insulating material such as synthetic resin, and is provided with a second electrode mounting portion 33 on which the second electrode pin 20 is mounted. The second electrode pin 20 includes an intermediate portion, a projecting portion, and an internal connecting portion 20b. The intermediate portion is covered by an insulating cover 34. The projecting portion projects from the second electrode mounting portion 33 and is configured as an external connector 20a to which a plug (not shown) is connected. And, the internal connecting portion 20b is buried in the second electrode mounting portion 33 and is electrically connected to an internal ring-shaped connection terminal 35 of the casing 14a.

A female screw 36 is provided at the proximal end portion of the inner surface of the casing 14a, and the connection terminal 35 and a fixing ring 37 are fixed to the female screw 36. An electrically conductive cylinder 38 is provided in the inner space of the casing 14a such that the conductive cylinder 38 is encircled with and coaxial to the ring-shaped connection terminal 35, and the conductive cylinder 38 is electrically connected to the terminal 35. A ring-shaped probe holding member 39 is provided at the inner end portion of the conductive cylinder 38, and the probe holding member 39 is made of electrically conductive and elastic material such as an electrically conductive silicone rubber. When the probe 29 of the transducer unit 13 is inserted into the tubular member of the insertion sheath 22 and the transducer casing 26 of the transducer unit 13 is fit into the transducer unit connector 15 of the operation area main body 14, the probe holding member 39 closely contacts the probe 29 to electrically connect the probe 29 with the second electrode pin 20.

A cylindrical slider mounting member 40 which is made of electrically insulating material is provided on the outer surface of the conductive cylinder 38.

As shown in FIG. 3, a connection cylinder 41 is detachably connected to the inner end portion of the slider mounting member 40 by a connection pin 42, and a main channel tube 42a into which the probe 29 is inserted is connected to the inner end portion of the connection cylinder 41. The main channel tube 42a is inserted into the tubular member of the insertion sheath 22. A cylindrical electrically conductive member 43 is provided at the proximal end portion of the tubular member. The conductive member 43 is electrically connected to a cylindrical electrically conductive extending portion 44 through an electrically conductive rubber 170, and the extending portion 44 covers the outer circumferential surface of the slider mounting member 40.

The first electrode pin 19 which projects from the casing 14a of the operation area main body 14 includes an intermediate portion 19a, an external connecting portion 19b, and a proximal end portion. The intermediate portion 19a is covered by an electrically insulating cover 45. The external connector 19b projects outward from the casing 14a and is connected to a plug (not shown). And, the proximal end portion has an internal connection pin 46 buried in the casing 14a.

As shown in FIG. 4, the midpoint of a contact plate 47 formed by bending a plate spring to substantially C-shape is fixed to the internal connection pin 46. Contacts 47a are provided on the both end portions of the contact plate 47, and the contacts 47a are elastically in contact with two diametrically separated portions on the outer circumferential surface of the conductive extending portion 44. That is, the first electrode pin 19 is electrically connected to the conductive extending portion 44 of the conductive member 43 through the contact plate 47, and further electrically connected from the conductive member 43 to the insertion sheath 22.

As shown in FIGS. 2 and 3, a slider 48 is provided on the outer circumferential surface of the slider mounting member 40 provided in the inner space of the casing 14a of the operation area main body 14, and the slider 48 is slidable in the longitudinal direction of the slider mounting member 40. The slider 48 is urged by a spring 49 toward the proximal end portion of the inner space of the casing 14a of the operation area main body 14. A connection pin 50 connects the slider 48 to the movable handle 18 pivotally connected to the casing 14a of the operation area main body 14 by the pivot 17. By rotationally moving the movable handle 18, the slider mounting member 40 is moved forward and backward on the outer surface of the conductive cylinder 38, through the connection pin 50 and slider 48. This movement is transmitted to a drive rod 51 inserted in the tubular member of the insertion sheath 22, through the connection cylinder 41. That is, by moving the movable handle 18 in a direction indicated an arrow F, the drive rode 51 is moved forward in the tubular member of the insertion sheath 22.

Figure 7:
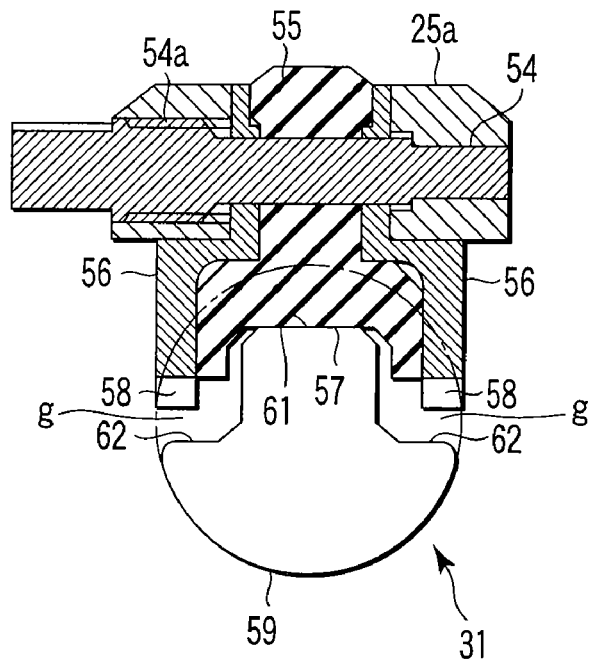
FIG. 7 is a transverse sectional view showing a state that a first grasping member of FIG. 6C is combined with a second grasping member.

Next, the surgical treatment area 23 will be explained with reference to FIGS. 5A to 7. FIG. 5A is a plan view of the surgical treatment area of the surgical instrument of FIG. 1. FIG. 5B is a longitudinal sectional view of the surgical treatment area of FIG. 5A. FIG. 6A is a transverse sectional view along a line of VIA-VIA in FIG. 5B. FIG. 6B is a transverse sectional view along a line of VIB-VIB in FIG. 5B. FIG. 6C is a transverse sectional view along a line of VIC-VIC in FIG. 5B. And, FIG. 7 is a transverse sectional view showing a state that a first grasping member of FIG. 6C is combined with a second grasping member.

The first grasping member 25 which is pivotally fixed by the pivot pin 24 to the holding member 22a provided at the distal end portion of the tubular member of the insertion sheath 22, is curved a little to the left side from the center of the axis of the insertion sheath 22 in the plane view as shown in FIG. 5A, so as to easily grasp a living tissue. The first grasping member 25 includes a grasping member main body 25a pivotally supported by the holding member 22a, and an ultrasonic surgical treatment area member 25b located in the distal end side of the grasping member main body 25a. A connection pin 53 is provided at the proximal end portion of the grasping member main body 25a, and the distal end portion of the drive rod 51 in the tubular member of the insertion sheath 22 is connected to the connection pin 53.

The distal end portion of the grasping member main body 25a is bifurcated. The ultrasonic surgical treatment area member 25b is pivotally supported in the cutout 51a of the bifurcated distal end portion of the grasping member main body 25a by a pivot pin 54 whose screw portion 54a is inserted into and fixed to the bifurcated distal end portion, and the ultrasonic surgical treatment area member 25b is rotational in a direction crossing the center of the insertion sheath 22. Therefore, the ultrasonic surgical treatment area member 25b is rotationally movable in the same direction as the first grasping member 25.

The ultrasonic surgical treatment area member 25b includes a pad member 55 forming a pressing portion, and a pair of first electrodes 56 provided symmetrically on both sides of the pad member 55. The pad member 55 is made of a low-friction material such as PTFE (polytetrafluoroethylene), and a square groove 57 is formed in its surface which is used to grasp a living tissue. A row of substantially sawtooth-like teeth 58 is formed on the surface of each first electrode 56, which is used to grasp the living tissue. The row of teeth 58 makes the surface of each first electrode 56 grasp the living tissue without slipping. The row of teeth 58 projects further outward from the grasping surface of the pad member 55 in a direction crossing the grasping surface of the pad member 55.

The first grasping member 25 configured as described above faces the ultrasonic vibrating portion 31 at the distal end portion of the probe 29 projected forward from the holding member 22a when the probe 29 of the transducer unit 13 is inserted into the insertion sheath 22. The ultrasonic vibrating portion 31 configures a second grasping member 59 which cooperates with the first grasping member 25 to grasp a living tissue. The second grasping member 59 is provided by machining the ultrasonic vibrating portion 31 which has conventionally a circular cross section at the distal end portion of the probe 29, into a non-circular cross section (a generally reversed T-shape) by a well-known machining such as forging, cutting, and the like. Specifically, a grasping surface 61 opposite to the square groove 57 of the pad member 55 of the ultrasonic surgical treatment area member 25b of the first grasping member 25, and a pair of second electrodes 62 opposite to the rows of teeth 58 of the pair of first electrodes 56 of the ultrasonic surgical treatment area member 25b are provided on the surface of the second grasping member 59 opposite to the first grasping member 25.

In the second grasping member 59, the pair of second electrodes 62 is located farther from the ultrasonic surgical treatment area member 25b of the first grasping member 25, than the grasping surface 61, and makes a step to the grasping surface 61. Further, each second electrode 62 forms a gap "g" to each row of teeth 58 of each first electrode 56 of the ultrasonic surgical treatment area member 25b, when the grasping surface 61 contacts the bottom surface of the square groove 57 of the pad member 55 of the ultrasonic surgical treatment area member 25b of the first grasping member 25. This gap "g" prevents a short circuit between the first electrode 56 and second electrode 62.

That is, when the first grasping member 25 is pivotally moved in a direction where it approaches the second grasping member 59 (grasping operation), the grasping surface 61 of the second grasping member 59 contacts the bottom surface of the square groove 57 of the pad member 55 of the ultrasonic surgical treatment area member 25b of the first grasping member 25, but each second electrode 56 comes close to but faces each row of teeth 58 of each first electrode 56 of the ultrasonic surgical treatment area member 25b with the gap "g" therebetween.

When the first grasping member 25 is rotated around the pivot pin 24 in a direction where it approaches the second grasping member 59 by the operation of the drive rod 51 in the insertion sheath 22, and the first grasping member 25 is placed at a position to grasp a living tissue in cooperation with the second grasping member 59, the bottom surface of the square groove 57 of the first grasping member 25 and the grasping surface 61 of the second grasping member 59 are in contact with each other to form a cut-join face, and the rows of teeth 58 of the pair of first electrodes 56 and the pair of second electrodes 62 are faced each other and placed in parallel to each other to form a pair of coagulate-join faces.

Since the cut-join face and the pair of coagulate-join faces extend in a direction orthogonal to the opening/closing direction of the first and second grasping members 25 and 59, the first and second grasping members 25 and 59 can provide a strong grasping force to a living tissue.

Further, since the cut-join face and the pair of coagulate-join faces are arranged to separate from each other in the direction orthogonal to the opening/closing direction of the first and second grasping members 25 and 59, the second grasping member 59 configured by the ultrasonic vibrating portion 31 at the distal end portion of the probe 29 does not project from the first grasping member 25 in both sides thereof in the direction orthogonal to the above opening/closing direction. Therefore, the surgical treatment area 23 can be easily inserted into a narrow portion in a body cavity and can perform a treatment thereto.

Next, an operation of the surgical instrument 10 configured as described above will be explained.

For example, when performing a surgical treatment for the purpose of sealing a blood vessel in an abdominal cavity of a patient, the insertion area 12 of the surgical instrument 10 is inserted into the abdominal cavity of the patient through a trocar (not shown) inserted into an opening formed in an abdomen of the patient. Then, the surgical treatment area 23 at the distal end portion of the insertion area 12 is approached a part of the blood vessel where the surgical treatment will be performed.

When the movable handle 18 is not moved in the direction indicated by the arrow F in FIG. 2 with respect to the fixed handle 16, the drive rod 51 is retracted in the tubular member of the insertion sheath 22 by the urging force of the spring 49 in the casing 14a of the operation area main body 14 of the operation area 11, and the first grasping member 25 can be placed at the open position far from the second grasping member 59.

After placing the part of the blood vessel where the surgical treatment will be performed between the second grasping member 59 and the first grasping member 25 placed at the opening position, the movable handle 18 is pivotally moved in the direction indicated by the arrow F in FIG. 2 with respect to the fixed handle 16 of the operation area 11. At this time, the drive rod 51 connected to the slider holding member 40 through the connection cylinder 41 can be advanced in the tubular member of the insertion sheath 22 against the urging force of the spring 49 in the casing 14a of the operation area main body 14 of the operation area 11. The advanced drive rod 51 pivotally moves the first grasping member 25 toward the second grasping member 59 around the pivot pin 24.

Figure 8:
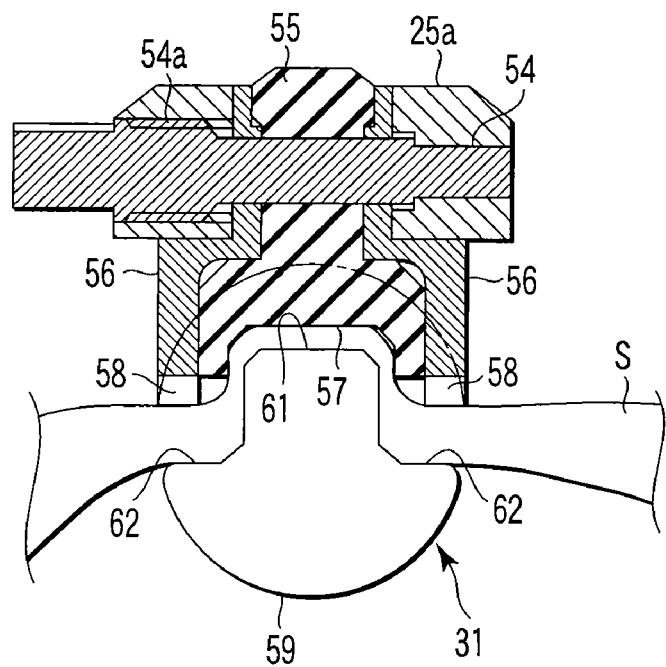
FIG. 8 is a transverse sectional view showing a state that a living tissue is grasped by the first and second grasping members of the surgical treatment area of FIG. 7.

As a result, as shown in FIG. 8, a living tissue S of the part of the blood vessel where the surgical treatment will be performed is grasped between the first and second grasping members 25 and 59. That is, the tissue S is grasped in the cut-join face between the grasping surface 61 of the second grasping member 59 and the bottom surface of the square groove 57 of the pad member 55 of the ultrasonic surgical treatment area member 25b of the first grasping member 25, and is also grasped in the coagulate-join faces between the pair of first electrodes 56 on both sides of the square groove 57 of the bad member 55 and the pair of second electrodes 62 on both sides of the grasping surface 61 of the second grasping member 59. In this time, since each of the cut-join face and coagulate-join faces extends in the direction orthogonal to the grasping direction of the first and second grasping members 25 and 59, the tissue S can be grasped by a strong force. Moreover, the rows of teeth 58 provided on the pair of first electrodes 56 prevents the tissue S from slipping and escaping from the grasping members.

When the ultrasonic transducer in the transducer casing 26 of the transducer unit 13 is driven in this state, the ultrasonic vibration generated by the ultrasonic transducer is transmitted to the ultrasonic vibrating portion 31 at the distal end portion of the probe 29 through the probe 29, and the second grasping member 59 configured by the ultrasonic vibrating portion 31 is ultrasonically vibrated. This ultrasonic vibration generates a frictional heat in the part of the tissue S grasped between the grasping surface 61 of the second grasping member 59 and the bottom surface of the square groove 57 of the pad member 55 of the ultrasonic surgical treatment area member 25b of the first grasping member 25, and this part of the tissue S is coagulated by the frictional heat, and cut further.

Next, a high-frequency current is applied from a not shown high-frequency power supply to the first electrode pin 19 of the operation area 11. The high-frequency current is led to the tubular member of the insertion sheath 22 through the contact plate 47, conductive extending portion 44, conductive rubber 170 and conductive member 43 in the casing 14a of the operation area main body 14 of the operation area 11, and reaches the pair of first electrodes 56 of the ultrasonic surgical treatment area member 25b of the first grasping member 25. The high-frequency current is further led from the pair of first electrodes 56 to the pair of second electrodes 62 of the second grasping member 59 through the tissue S, and returned from the ultrasonic vibrating portion 31 at the distal end portion of the probe 29 forming the second grasping member 59 and the probe 29, to the above-mentioned high-frequency power supply, through the probe holding member 39, conductive cylinder 38, connection terminal 35 and second electrode pin 20 in the casing 14a of the operation area main body 14 of the operation area 11.

The pair of the portions of the tissue S, where high-frequency current flows between the pair of first electrodes 56 of the ultrasonic surgical treatment area member 25b of the first grasping member 25 and the pair of second electrodes 62 of the second grasping member 59, is coagulated.

The tissue S grasped between the first grasping member 25 and the second grasping member 59 is cut at the portion grasped between the grasping surface 61 of the second grasping member 59 and the bottom surface of the square groove 57 of the pad member 55 of the ultrasonic surgical treatment area member 25b of the first grasping member 25, and the pair of the portions of the tissue S grasped between the pair of second electrodes 62 of the second grasping member 59 and the pair of first electrodes 56 of the ultrasonic surgical treatment area member 25b of the first grasping member 25 is coagulated.

Since the tissue S is a part of the blood vessel to be surgically treated, the above-mentioned part of the blood vessel is cut at the portion grasped between the grasping surface 61 of the second grasping member 59 and the bottom surface of the square groove 57 of the pad member 55 of the ultrasonic surgical treatment area member 25b of the first grasping member 25, and is coagulated, that is, sealed at the pair of the portions grasped between the pair of second electrodes 62 of the second grasping member 59 and the pair of first electrodes 56 of the ultrasonic surgical treatment area member 25b of the first grasping member 25.

When the first grasping member 25 grasps the tissue S in cooperation with the second grasping member 59, the grasping surface 61 of the second grasping member 59 makes a surface contact with the bottom surface of the square groove 57 of the pad member 55 of the ultrasonic surgical treatment area member 25b of the first grasping member 25 and forms the cut-join face, and the rows of teeth 58 of the pair of first electrodes 56 of the ultrasonic surgical treatment area member 25b face the pair of second electrodes 62 of the second grasping member 59 in substantially parallel thereto and form the coagulate-join face, thereby the tissue S can be grasped by a sufficiently strong force. Therefore, the coagulation and cutting ability can be increased by using both ultrasonic vibration and high-frequency current, and the surgical treatment time in the surgical treatment area 23 can be reduced.

The ultrasonic vibration and the high frequency current be used at the same time. The ultrasonic vibration may be preferentially used when the cutting is prior to the coagulation, and the high-frequency current may be preferentially used when the coagulation is prior to the cutting.

Figure 9B:
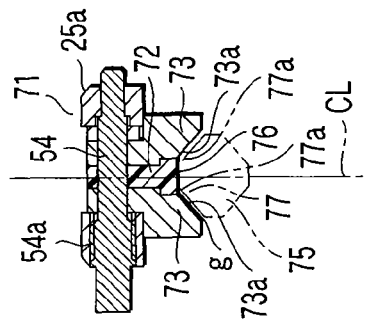
FIG. 9B is a transverse sectional view along a line of IXB-IXB in FIG. 9A.

Next, a surgical instrument according to a second embodiment of the invention will be explained with reference to FIGS. 9A and 9B. In the second embodiment, the same components as those of the first embodiment described above with reference to FIG. 1 to FIG. 8 will be denoted by the same reference numerals and detailed explanation thereof will be omitted.

Figure 9A:
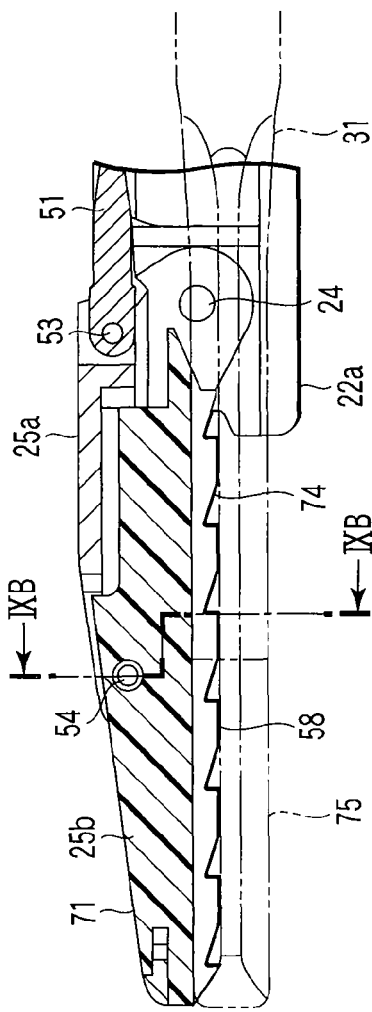
FIG. 9A is a longitudinal sectional view of a surgical treatment area of a surgical instrument according to a second embodiment of the invention.

FIG. 9A is a longitudinal sectional view of a surgical treatment area of the surgical instrument according to the second embodiment of the present invention. FIG. 9B is a transverse sectional view along a line of IXB-IXB in FIG. 9A.

In this embodiment, in a pair of first electrodes 73 on both sides of a pad member 72 in the ultrasonic surgical treatment area member 25b of a first grasping member 71, each of a pair of surface areas to face a pair of second electrodes 75 of a second grasping member 75 is inclined (to 45°, for example) to form an inclined surface 73a with respect to a line CL passing the center of the pad member 72 and extending along the pivotal movement direction of the first grasping member 71. A row of substantially sawtooth-like teeth 74 is formed at the outer end portion of the inclined surface 73a of each first electrode 73 to grasp a living tissue without slipping.

Further, in this embodiment, the second grasping member 75 is provided by machining the ultrasonic vibrating portion 31 which has conventionally a circular cross section, at the distal end portion of the probe 29, into a non-circular cross section (substantially an octagonal form), by a well-known machining such as forging, cutting and the like. The surface of the second grasping member 75 facing to the first grasping member 71 has a grasping surface 76 facing to the pad member 72 of the ultrasonic surgical treatment area member 25b of the first grasping member 71, and a pair of second electrodes 77 which faces the inclined surface 73a of the pair of first electrodes 73 of the ultrasonic surgical treatment area member 25b and which has inclined surfaces 77a inclined similarly to the inclined surfaces 73a.

When the grasping surface 76 of the second grasping member 75 contacts the facing surface of the pad member 72 of the ultrasonic surgical treatment area member 25b of the first grasping member 71, each inclined surface 77a of the pair of second electrodes 77 of the second grasping member 75 faces each inclined surface 73a of the pair of first electrodes 73 of the ultrasonic surgical treatment area member 25b of the first grasping member 71 with a gap "g" between them.

When the first grasping member 71 is pivotally moved around the pivot pin 24 in the direction in which the first grasping member 71 comes close to the second grasping member 75, and the first grasping member 71 is placed at a position where the first grasping member 71 grasps a living tissue in cooperation with the second grasping member 75 between them, the pad member 72 of the first grasping member 71 makes a surface contact with the grasping surface 76 of the second grasping member 75 and forms a cut-join face, and the inclined surfaces 73a of the pair of first electrodes 73 face the inclined surfaces 77a of the pair of second electrodes 77 in substantially parallel thereto and form a pair of coagulate-join faces.

Since the cut-join face extends in a direction orthogonal to the opening/closing direction of the first and second grasping members 71 and 75, and each coagulate-join face is inclined (to 45° for example) to the direction orthogonal to the above opening/closing direction, the first and second grasping members 71 and 75 can provide a strong grasping force for the living tissue.

Further, since the cut-join face and the pair of coagulate-join faces are arranged to separate from each other in the direction orthogonal to the opening/closing direction of the first and second grasping members 71 and 75, the second grasping member 75 configured by the ultrasonic vibrating portion 31 at the distal end portion of the probe 29 is not projected from the first grasping member 71 in its both sides in the direction orthogonal to the above opening/closing direction. Therefore, the surgical treatment area 23 can be easily inserted into a narrow portion of an abdominal cavity and treat it.

Figure 10B:
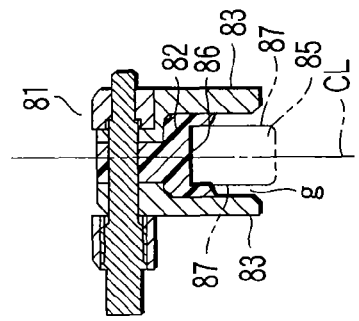
FIG. 10B is a transverse sectional view along a line of XB-XB in FIG. 10A.

Next, a surgical instrument according to a third embodiment of the invention will be explained with reference to FIGS. 10A and 10B. In the third embodiment, the same components as those of the first embodiment described above with reference to FIGS. 1 to 8 will be denoted by the same reference numerals and detailed explanation thereof will be omitted.

Figure 10A:
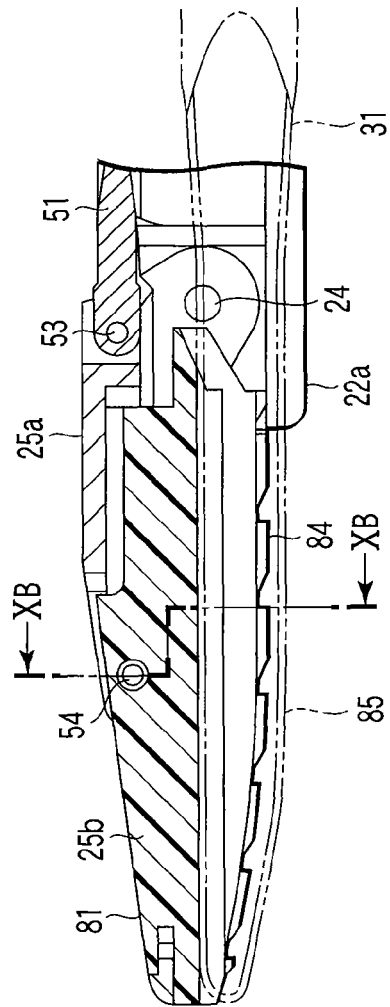
FIG. 10A is a longitudinal sectional view of a surgical treatment area of a surgical instrument according to a third embodiment of the invention.

FIG. 10A is a longitudinal sectional view of a surgical treatment area of the surgical instrument according to a third embodiment of the invention. FIG. 10B is a transverse sectional view along a line of XB-XB in FIG. 10A.

In this embodiment, a pair of first electrodes 83 in both sides of a pad member 82 in the ultrasonic surgical treatment area member 25b of a first grasping member 81 is projected along and in parallel to a line CL passing the center of the pad member 82 and extending along the moving direction of the first grasping member 81. A row of substantially sawtooth-like teeth 84 is formed on each projected end surface of the pair of first electrodes 83 to grasp a living tissue without slipping.

Further, in this embodiment, a second grasping member 88 is provided by machining the ultrasonic vibrating portion 31, which has conventionally the circular cross section, at the distal end portion of the probe 29, into a non-circular cross section (rectangular), by a well-known machining such as forging, cutting, and the like. The surface of the second grasping member 85 which faces the first grasping member 81 has a grasping surface 86 which faces a pad member 82 of the ultrasonic surgical treatment area member 25b of the first grasping member 81, and a pair of second electrodes 87 which face the inside surfaces of the pair of first electrodes 83 of the ultrasonic surgical treatment area member 25b.

When the grasping surface 86 of the second grasping member 85 contacts the facing surface of the pad member 82 of the ultrasonic surgical treatment area member 25b of the first grasping member 81, each second electrode 87 of the second grasping member 85 faces each inside surface of the pair of first electrodes 83 of the ultrasonic surgical treatment area member 25b of the first grasping member 81 with a gap "g" therebetween.

When the first grasping member 81 is pivotally moved around the pivot pin 24 in the direction in which the first grasping member 81 comes close to the second grasping member 85 and placed at a position where the first grasping member 81 grasps a living tissue in cooperation with the second grasping member 85, the pad member 82 of the first grasping member 81 makes a surface contact with the grasping surface 86 of the second grasping member 85 and forms a cut-join face, and the inside surfaces of the pair of first electrodes 83 face the pair of second electrodes 87 in substantially parallel thereto and form a pair of coagulate-join faces.

Since the cut-join face extends in the direction orthogonal to the opening/closing direction of the first and second grasping members 81 and 85, and the pair of coagulate-join faces extends in parallel to the above opening/closing direction, the first and second grasping members 81 and 85 can provide a strong grasping force for a living tissue.

Further, since the cut-join face and the pair of coagulate-join faces are separated from each other in the direction orthogonal to the opening/closing direction of the first and second grasping members 81 and 85, the second grasping member 85 configured by the ultrasonic vibrating portion 31 at the distal end portion of the probe 29 does not project from the first grasping member 81 in its both sides in the direction orthogonal to the above opening/closing direction. Therefore, the surgical treatment area 23 can be easily inserted into a narrow portion in an abdominal cavity and treat it.

Figure 11B:
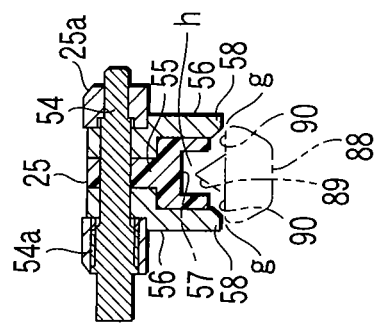
FIG. 11B is a transverse sectional view along a line of XIB-XIB in FIG. 11A.

Next, a surgical instrument according to a fourth embodiment of the invention will be explained with reference to FIGS. 11A and 11B. In the fourth embodiment, the same components as those of the first embodiment described above with reference to FIGS. 1 to 8 will be denoted by the same reference numerals and detailed explanation thereof will be omitted.

Figure 11A:
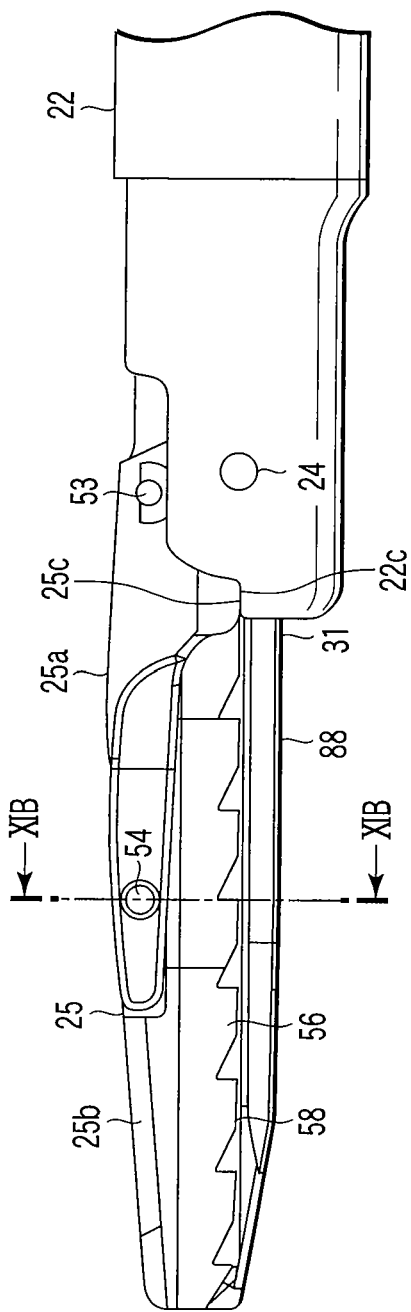
FIG. 11A is a longitudinal sectional view of a surgical treatment area of a surgical instrument according to a fourth embodiment of the invention.

FIG. 11A is a longitudinal sectional view of a surgical treatment area of a surgical instrument according to a fourth embodiment of the invention. FIG. 11B is a transverse sectional view along a line of XIB-XIB in FIG. 11A.

In this embodiment, only a second grasping member 88 is different from the first embodiment. The second grasping member 88 is provided by machining the ultrasonic vibrating portion 31 which has a conventionally circular cross section, at the distal end portion of the probe 29, into a non-circular cross section (substantially a reversed T-shape), by a well-known machining such as forging, cutting, and the like. The cross section of the second grasping member 59 of the first embodiment shown in FIGS. 7 and 8 is also a reversed T-shape. But, the cross section of the second grasping member 88 of the fourth embodiment is slightly different from that of the second grasping member 59 of the first embodiment. Specifically, a portion of the second grasping member 88 of the fourth embodiment, which project from the midpoint of the laterally extending surface of the second grasping member 88, the laterally extending surface facing the first grasping member 25, in the direction crossing the lateral direction, and which is inserted into the square groove 57 of the pad member 55 of the ultrasonic surgical treatment member 25b of the first grasping member 25, is formed to have a triangular shape having an acute angle at its projected end.

In the cross section of the facing surface of the second grasping member 88 of the fourth embodiment, the above described triangular portion forms a grasping surface 89, and a pair of portions extending laterally in both sides of the grasping surface 89 forms a pair of flat second electrodes 90 which face the pair of first electrodes 56 (the rows of teeth 58) of the ultrasonic surgical treatment area member 25b of the first grasping member 25.

When the first grasping member 25 is pivotally moved around the pivot pin 24 in the direction in which the first grasping member 25 comes close to the second grasping member 88 and a contact portion 25c of the grasping part main body 25a contacts a contact portion 22c of the holding member 22a at the distal end portion of the insertion sheath 22, a gap "h" is formed between the acute projected end of the grasping surface 89 of the second grasping member 88 and the bottom surface of the square groove 57 of the pad member 55 of the ultrasonic surgical treatment area member 25b of the first grasping member 25, and a gap "g" is formed between each second electrode 90 of the second grasping member 88 and each first electrode 56 (the row of teeth 58) of the ultrasonic surgical treatment area member 25b of the first grasping member 25.

When the first grasping member 25 is pivotally moved around the pivot pin 24 in the direction in which the first grasping member 25 comes close to the second grasping member 88 and placed at a position where the first grasping member 25 grasps a living tissue in cooperation with the second grasping member 88, the acute end of the grasping surface 89 of the second grasping member 88 extends to the bottom surface of the square groove 57 of the pad member 55 of the first grasping member 25 in a direction orthogonal to the center line of the pivot pin 24 of the first grasping member 25 and forms a cut-join line, and the pair of first electrodes 56 and the pair of second electrodes 90 face each other in substantially parallel to each other and form a pair of coagulate-join faces.

Since the cut-join line extends in the direction orthogonal to the center line of the pivot pin 24 of the first grasping member 25 and the pair of coagulate-join faces extends in the direction orthogonal to the opening/closing direction of the first and second grasping members 25 and 88, the first and second grasping members 25 and 88 can provide a strong grasping force for a living tissue.

Further, since the cut-join line and the pair of coagulate-join faces are separated from each other in the direction orthogonal to the opening/closing direction of the first and second grasping members 25 and 88, the second grasping member 88 configured by the ultrasonic vibrating portion 31 at the distal end portion of the probe 29 does not project from the first grasping member 25 in both sides thereof in the direction orthogonal to the above opening/closing direction. Therefore, the surgical treatment area 23 can be easily inserted into a narrow portion in an abdominal cavity and treat it.

In this embodiment, since the acute end of the grasping surface 89 of the second grasping member 88 does not contact the bottom surface of the square groove 57 of the pad member 55 of the first grasping member 25, the bottom surface of the square groove 57 of the pad member 55 is not worn by the grasping surface 89 of the second grasping member 88, and the durability of this embodiment increases.

The cut-join line formed by making the acute end of the grasping surface 89 of the second grasping member 88 in contact with the bottom surface of the square groove 57 of the pad member 55 of the first grasping member 25 generates a large concentration of grasping force for a living tissue grasped between the grasping surface 89 of the second grasping member 88 and the bottom surface of the square groove 57 of the pad member 55 of the first grasping member 25.

Next, a surgical instrument according to a fifth embodiment of the invention will be explained with reference to FIGS. 12A and 12B. In the fifth embodiment, the same components as those of the first embodiment described above with reference to FIG. 1 to FIG. 8 will be denoted by the same reference numerals and detailed explanation thereof will be omitted.

Figure 12A:
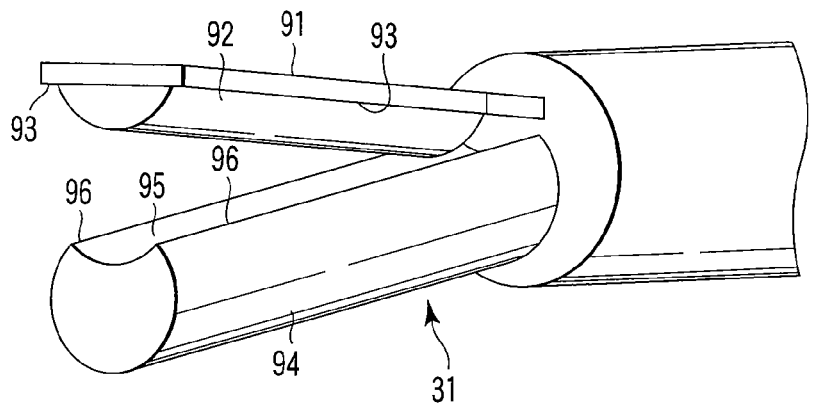
FIG. 12A is a schematic perspective view of a surgical treatment area of a surgical instrument according to a fifth embodiment of the invention.
Figure 12B:
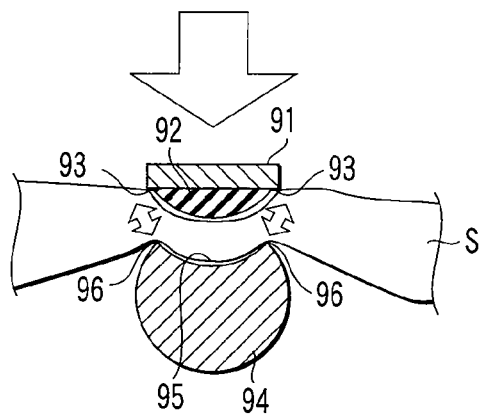
FIG. 12B is a transverse sectional view showing a state that a living tissue is grasped by first and second grasping members of the surgical treatment area of FIG. 12A.

FIG. 12A is a schematic perspective view of a surgical treatment area of a surgical instrument according to a fifth embodiment of the invention. FIG. 12B is a transverse sectional view showing a state in which a living tissue is grasped by first and second grasping members of the surgical treatment area of FIG. 12A.

In this embodiment, a first grasping member 91 is formed like a flat plate. A pad member 92 having an arc-shaped cross section is provided at a mid portion of a flat grasping surface of the first grasping member 91 in a lateral direction thereof. A pair of first electrodes 93 is provided in both sides of the pad member 92 on the above grasping surface.

A second grasping member 94 is provided by machining the ultrasonic vibrating portion 31 which has conventionally a circular cross section, at the distal end portion of the probe 29, into a non-circular cross section, by a well-known machining such as forging, cutting, and the like. Specifically, a grasping surface 95 having an concave cross section is provided in a portion of the second grasping member 94 which faces the first grasping member 91, the grasping surface 95 corresponding to the pad member 92 of the first grasping member 91. A pair of second electrodes 96 is provided at both edge portions of the grasping surface 95 in its cross section to face the pair of first electrodes 93 of the first grasping member.

When the first grasping member 91 is pivotally moved in the direction in which the first grasping member 91 comes close to the second grasping member 94 and placed at a position where the first grasping member 91 grasps a living tissue in cooperation with the second grasping member 94, the pad member 92 of the first grasping member 91 makes a surface contact with the grasping surface 95 of the second grasping member 88 and forms a curved cut-join face, and the acute ends of the pair of second electrodes 96 face the pair of first flat electrode 93 and form a pair of coagulate-join lines extending in a direction orthogonal to the center line of the pivotal movement of the first grasping member 91.

The pair of coagulate-join lines formed by the pair of first flat electrodes 93 of the first grasping member 91 and the acute ends of the pair of second electrodes 96 at the both side edges of the grasping surface 95 of the second grasping member 94, generates a large concentration of grasping force for the tissue S grasped by the pad member 92 of the first grasping member 91 and the grasping surface 95 of the second grasping member 94.

In this embodiment, the first grasping member 91 can be made more compact that the second grasping member 94 configured by the ultrasonic vibrating portion 31 at the distal end portion of the probe 29. Therefore, the surgical treatment area 23 can be easily inserted into a narrow portion in an abdominal cavity and treat it.

Next, a surgical instrument according to a sixth embodiment of the present invention will be explained with reference to FIG. 13. In the sixth embodiment, the same components as those of the first embodiment described above with reference to FIG. 1 to FIG. 8 will be denoted the same reference numerals and detailed explanation thereof will be omitted.

Figure 13:
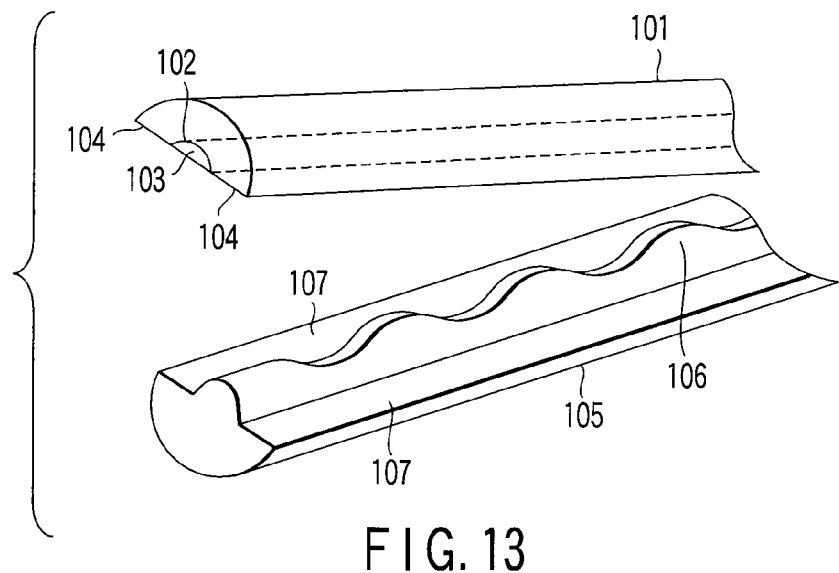
FIG. 13 is a schematic perspective view of a surgical treatment area of a surgical instrument according to a sixth embodiment of the invention.

FIG. 13 is a schematic perspective view of a surgical treatment area of the surgical instrument according to the sixth embodiment of the present invention.

In this embodiment, a first grasping member 101 has a semicircular cross section, and a pad member 103 is buried in a rounded groove 102 made at the lateral center of the surface of the first grasping member 101, the surface facing a second grasping member 105. A pair of first flat electrodes 104 is provided in both sides of the pad member 103 on the facing surface of the first grasping member 101.

The second grasping member 105 is provided by machining the ultrasonic vibrating portion 31 which has conventionally a circular cross section, at the distal end portion of the probe 29, into a non-circular cross section, by a well-known machining such as forging, cutting, and the like. Specifically, a grasping surface 106 projecting toward the pad member 103 of the facing surface of the first grasping member 101 and a pair of second flat electrodes 107 arranged in both sides of the grasping surface 106 and facing the pair of first flat electrodes 104 of the facing surface of the first grasping member 101 are provided on a part of the second grasping member 105 facing the first grasping member 101. The grasping surface 106 is shaped like waves gently continuing along the extending direction of the pad member 10.

When the first grasping member 101 is pivotally moved in the direction in which the first grasping member 101 comes close to the second grasping member 105 and placed at a position where the first grasping member 101 grasps a living tissue in cooperation with the second grasping member 105, the pad member 103 of the first grasping member 101 discontinuously contacts the gently continuing wave-shaped grasping surface 106 of the second grasping member 105 and forms a cut-join face, and the pair of second flat electrodes 107 face the pair of first flat electrodes 104 in parallel thereto and form a pair of coagulate-join faces which are extending in the direction orthogonal to the center line of the opening/closing direction of the first grasping member 101.

The above described cut-join face and pair of coagulate-join faces can provide a strong grasping force for the tissue between the first grasping member 101 and second grasping member 105. In this embodiment, it is unnecessary to provide a row of teeth for anti-slipping on each of the pair of first electrodes 104, and the pair of first electrodes 104 can minutely coagulate the tissue in cooperation with the pair of second electrodes 107.

Next, a surgical instrument according to a seventh embodiment of the invention will be explained with reference to FIGS. 14A and 14B. In the seventh embodiment, the same components as those of the first embodiment described above with reference to FIGS. 1 to 8 will be denoted by the same reference numerals and detailed explanation thereof will be omitted.

Figure 14A:
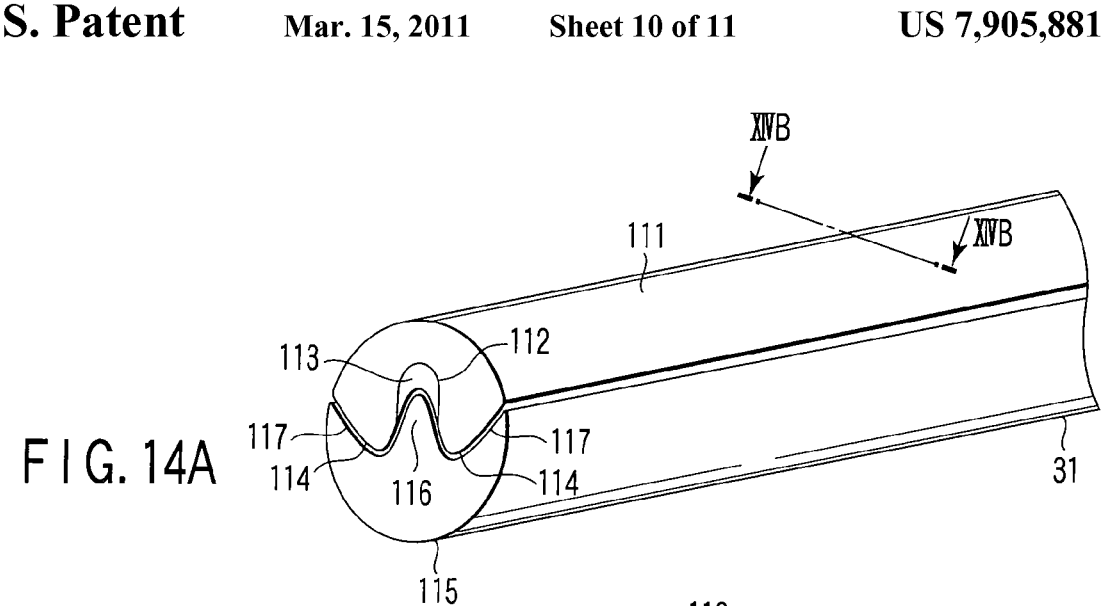
FIG. 14A is a schematic perspective view of a surgical treatment area of a surgical instrument according to a seventh embodiment of the invention.

FIG. 14A is a schematic perspective view of a surgical treatment area of the surgical instrument according to the seventh embodiment of the invention.

Figure 14B:
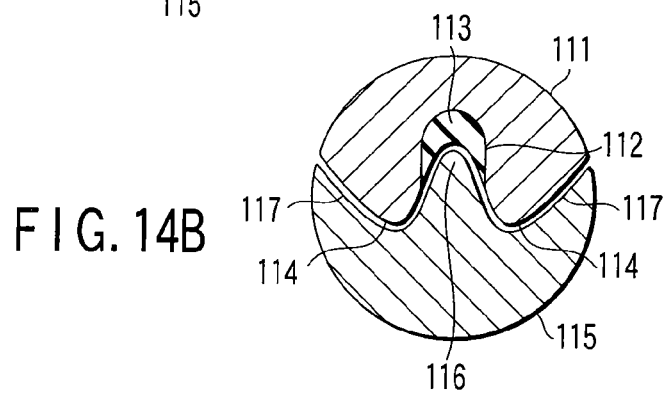
FIG. 14B is a transverse sectional view along a line of XIVB-XIVB in FIG. 14A.

FIG. 14B is a transverse sectional view along a line of XIVB-XIVB in FIG. 14A.

In this embodiment, a first grasping member 111 has a cross section similar to a cross section of a saddle for riding a horse, and a pad member 113 is buried in a rounded groove 112 at the center of a surface of the first grasping member 111 in the lateral direction, the surface facing a second grasping member 115. In the opposite surface of the first grasping member 111, A pair of portions projected from both sides of the pad member 113 on the facing surface of the first grasping member 111 is configured as a pair of first electrodes 114.

The second grasping member 115 is provided by machining the ultrasonic vibrating portion 31 which has conventionally a circular cross section, at the distal end portion of the probe 29, into a non-circular cross section, by a well-known machining such as forging, cutting, and the like. Specifically, the surface of the second grasping member 115 which faces the first grasping member 111 is formed to have a cross section corresponding to the facing surface of the first grasping member 111.

That is, a portion of the facing surface of the second grasping member 115, the portion corresponding to the pad member 113 on the facing surface of the first grasping member 111, is configured as a grasping surface 116 projecting toward the pad member 113 and having a rounded substantially triangular cross section, and a pair of portions of the facing surface of the second grasping member 115, the portions corresponding to the pair of first electrodes 114 of the facing surface of the first grasping member 111, is configured as a pair of concaved second electrodes 117 to receive the pair of first projecting electrodes 114.

When the first grasping member 111 is pivotally moved in a direction in which the first grasping member 111 comes close to the second grasping member 115 and placed at a position where the first grasping member 111 grasps a living tissue in cooperation with the second grasping member 115, the pad member 113 of the first grasping member 111 makes a line contact with the grasping surface 116 of the second grasping member 115 and forms a cut-join face, and the pair of first electrodes 114 contacts the pair of second electrodes 117 in a wide area and forms a pair of coagulate-join faces.

Next, a surgical instrument according to an eighth embodiment of the present invention will be explained with reference to FIG. 15. In the eighth embodiment, the same components as those of the first embodiment described above with reference to FIGS. 1 to 8 will be denoted by the same reference numerals and detailed explanation thereof will be omitted.

Figure 15:
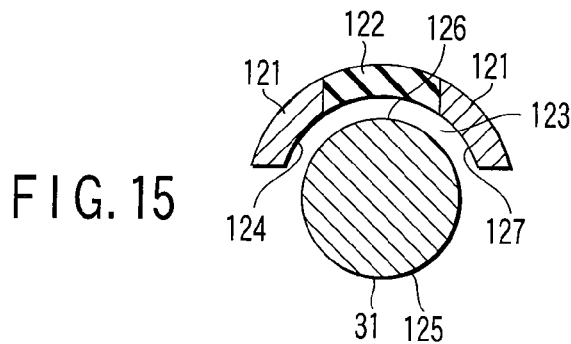
FIG. 15 is a schematic transverse sectional view of a surgical treatment area of a surgical instrument according to an eighth embodiment of the invention.

FIG. 15 is a schematic transverse sectional view of a surgical treatment area of the surgical instrument according to the eighth embodiment of the present invention.

In this embodiment, a first grasping member 121 has an arc-shaped cross section. A pad member 122 is provided at the center of the arc-shape, and first and second electrodes 124 and 127 are provided on both sides of the pad member 122. The inner surface 123 of the first grasping member 121 faces a second grasping member 125.

The second grasping member 125 is configured by the rounded bar-shaped ultrasonic vibrating portion 31 at the distal end portion of the probe 29. The portion of the outer circumferential surface of the second grasping member 125 facing the inner surface 123 of the first grasping member 121 forms a grasping surface 126.

When the first grasping member 121 is pivotally moved in a direction in which the first grasping member 121 comes close to the second grasping member 125 and placed at a position where the first grasping member 121 grasps a living tissue in cooperation with the second grasping member 125, the pad member 122 of the first grasping member 121 makes a surface contact with the grasping surface 126 of the second grasping member 125 and forms a cut-join face, and the first electrode 124 and the second electrode 127 facing each other through the pad member 122 form coagulate-join faces. The first electrode 124 and the second electrode 127 apply a high-frequency current to the living tissue grasped between the inner surface 123 of the first grasping member 121 and the grasping surface 126 of the second grasping member 125.

Next, a surgical instrument according to a ninth embodiment of the present invention will be described with reference to FIG. 16. In the ninth embodiment, the same components as those of the first embodiment described above with reference to FIG. 1 to FIG. 8 will be denoted by the same reference numerals and detailed explanation thereof will be omitted.

Figure 16:
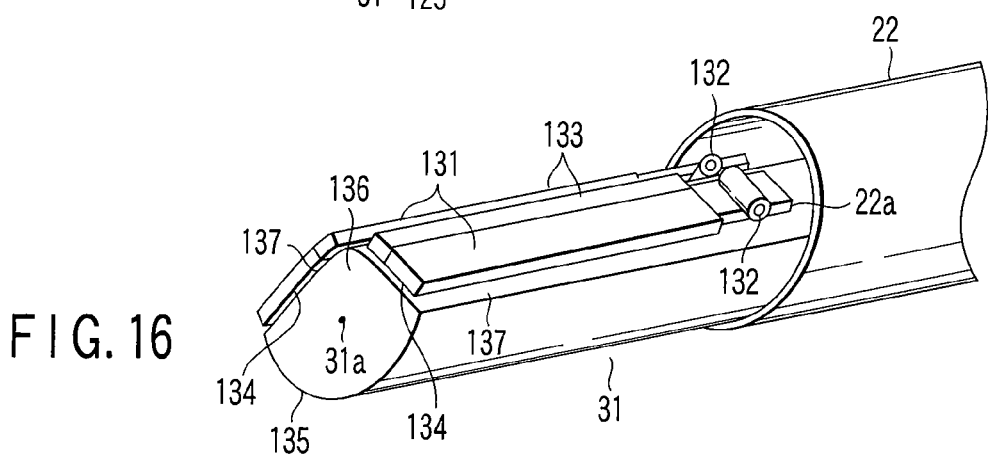
FIG. 16 is a schematic perspective view of a surgical treatment area of a surgical instrument according to a ninth embodiment of the invention.

FIG. 16 is a schematic perspective view of a surgical treatment area of the surgical instrument according to the ninth embodiment of the invention.

In this embodiment, a first grasping member 131 includes two independent parts. The two parts of the first grasping member 131 are pivotally connected to two surfaces of a holding member 22a having a triangular cross section, by pivots 132. Two edge portions of the two parts of the first grasping member 131 adjacent to each other are configured as pad members 133, and the inner surfaces of two edge portions of the two parts of the first grasping member 131 located away from each other are configured as first electrodes.

The second grasping member 135 is provided by machining the ultrasonic vibrating portion 31 which has conventionally a circular cross section, at the distal end portion of the probe 29, into a non-circular cross section, by a well-known machining such as forging, cutting, and the like. Specifically, a surface of the second grasping member 135 which faces the two parts of the first grasping member 131, is formed to correspond to the above described two surfaces of the holding member 22a having the triangular cross section.

A ridge portion of the triangular cross sectioned facing surface of the second grasping member 135, the ridge portion corresponding to the pad members 133 of the two adjacent edge portions of the first grasping member 131 is configured as a grasping surface 136, and the foot end portions of the triangular cross sectioned facing surface are configured as a pair of second electrodes 137.

When the two parts of the first grasping member 131 are pivotally moved to the second grasping member 135 in directions in which the two parts come close to the longitudinal center line 31a of the second grasping member 135 and placed at positions where the two parts grasp a living tissue in cooperation with the second grasping member 135, each of the pad members 133 of the two parts of the first grasping member 131 makes a surface contact with the grasping surface 136 of the second grasping member 135 and forms a cut-join face, and the first electrodes and the second electrodes 137 are faced each other and in parallel to each other, and form coagulate-join surfaces.

That is, since each of the opening/closing directions of the two parts of the first grasping member 131 is a radial direction of the second grasping member 135 that is the ultrasonic vibrating portion 31 at the distal end portion of the probe 29 and each of the pair of coagulate-join surfaces is formed in the direction orthogonal to each opening/closing direction, a strong grasping force can be proved for a living tissue on the pair of coagulate-join surfaces.

Next, a surgical instrument according to a tenth embodiment of the invention will be explained with reference to FIG. 17. In the tenth embodiment, the same components as those of the first embodiment described above with reference to FIGS. 1 to 8 will be denoted by the same reference numerals and detailed explanation thereof will be omitted.

Figure 17:
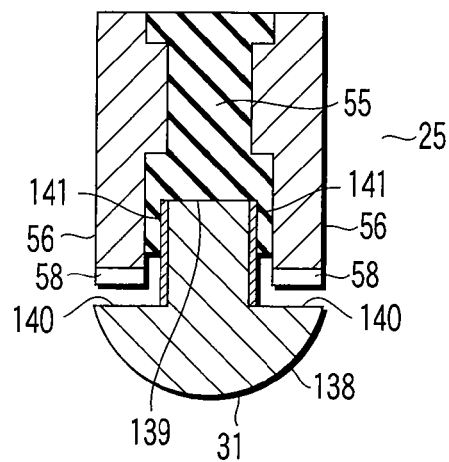
FIG. 17 is a schematic transverse sectional view of a surgical treatment area of a surgical instrument according to a tenth embodiment of the invention.

FIG. 17 is a schematic transverse sectional view of a surgical treatment area of the surgical instrument according to the tenth embodiment of the invention.

In this embodiment, only a second grasping member 138 is different from the first embodiment. The second grasping member 138 which grasps a living tissue in cooperation with the first grasping member 25, is provided by machining the ultrasonic vibrating portion 31 which has conventionally a circular cross section, at the distal end portion of the probe 29, into a non-circular cross section, by a well-known machining such as forging, cutting, and the like. Specifically, the surface of the second grasping member 138, which faces the first grasping member 25, includes a grasping surface 139 configured by a projecting portion facing the square groove 57 of the pad member 55 of the first grasping member 25, and a pair of second electrodes 140 having flat surfaces facing the pair of first electrodes 56 (the rows of teeth 58) in both sides of the grasping surface 139. When the projected end of the grasping surface 139 contacts the bottom surface of the square groove 57 of the pad member 55 of the first grasping member 25, each of the pair of second electrodes 140 is placed at a position where a gap "g" is forms between each of the pair of second electrodes 140 and each of the pair of first electrodes 56 (the rows of teeth 58). Further, insulating layers 141 are formed by insulation coating on both sides of the projected grasping surface 139 of the second grasping member 138, but the second electrodes 140 are not insulated by insulation coating. Therefore, the areas of the pair of first electrodes 56 can be substantially the same as those of the pair of second electrodes 140 and a current density therebetween can be increased, and a living tissue grasped therebetween can be efficiently coagulated.

Next, a surgical instrument according to an eleventh embodiment of the present invention will be explained with reference to FIG. 18. In the eleventh embodiment, the same components as those of the first embodiment described above with reference to FIGS. 1 to 8 will be denoted by the same reference numerals and detailed explanation thereof will be omitted.

Figure 18:
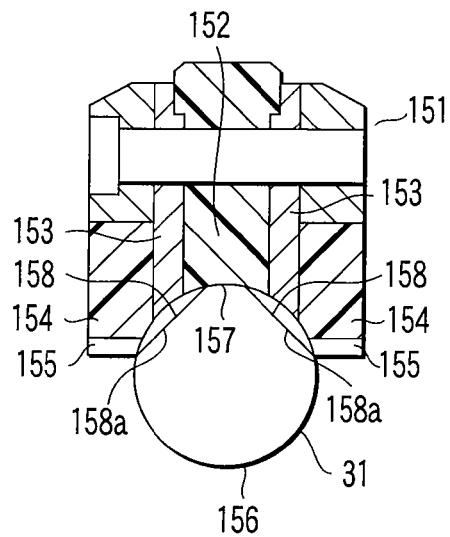
FIG. 18 is a schematic transverse sectional view of a surgical treatment area of a surgical instrument according to an eleventh embodiment of the invention.

FIG. 18 is a schematic transverse sectional view of a surgical treatment area of the surgical instrument according to the eleventh embodiment of the invention.

In a first grasping member 151 of this embodiment, an insulating block 154 made of synthetic resin is further integrally provided on an outside of each of a pair of first electrodes 153 on both sides of a pad member 152. The insulating block 154 is projected in the grasping direction from the first electrode 153. A row of teeth 155 is formed in the projected end of the insulating block 154.

A second grasping member 156 which grasps a living tissue in cooperation with the first grasping member 151 is provided by machining the ultrasonic vibrating portion 31 which has conventionally a circular cross section, at the distal end portion of the probe 29, into a non-circular cross section, by a well-known machining such as forging, cutting, and the like. Specifically, the surface of the second grasping member 156, which faces the first grasping member 151, is configured to a cross section of isosceles trapezoidal. The distal end of the second grasping member 156 is configured as a grasping surface 157 which is to be in contact with the pad member 152 of the first grasping member 151, and two legs on both sides of the grasping surface 157 are configured as a pair of second electrodes 158 having a pair of inclined surfaces 158a which face the pair of first electrodes 153.

When the first grasping member 151 is pivotally moved in a direction in which the first grasping member 151 comes close to the second grasping member 156 and placed at a position where the first grasping member 151 grasps a living tissue in cooperation with the second grasping member 156, the pad member 152 of the first grasping member 151 contacts the grasping surface 157 of the second grasping member 156 and forms a cut-join face. The pair of first electrodes 153 of the first grasping member 151 faces the pair of second electrodes 158 of the second grasping member 156 and forms a pair of coagulate-join faces. In this embodiment, even if a force directing in a lateral direction is applied to the ultrasonic vibrating portion 31 at the distal end portion of the probe 29, the vibrating portion 31 does not directly contact the pair of first electrodes 153. Therefore, the durability of the ultrasonic vibrating portion 31 at the distal end portion of the probe 29 is increased.

Next, an example of a surgical instrument which is different from the conventional one will be explained with reference to FIGS. 19A and 19B. In this example, the same components as those of the first embodiment described above with reference to FIGS. 1 to 8 will be denoted by the same reference numerals and detailed explanation thereof will be omitted.

Figure 19A:
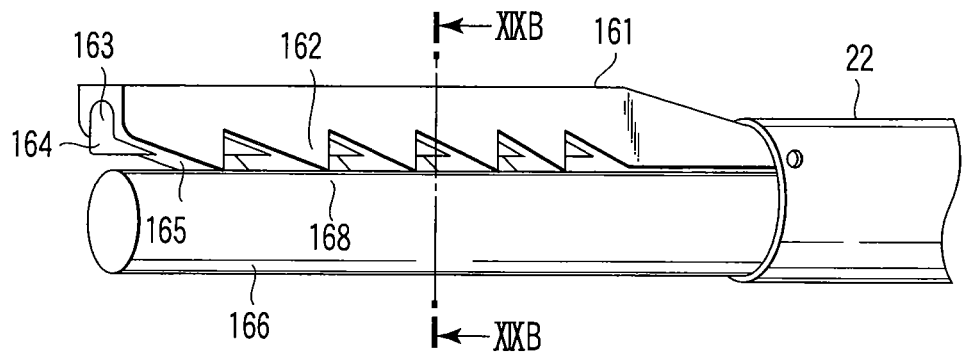
FIG. 19A is a schematic perspective view of a surgical treatment area of an example of a surgical instrument different from the conventional one.

FIG. 19A is a schematic perspective view of a surgical treatment area of the example of the surgical instrument which is different from the conventional one.

Figure 19B:
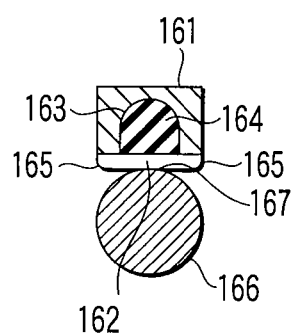
FIG. 19B is a schematic transverse sectional view along a line of XIX-XIX in FIG. 19A.

FIG. 19B is a schematic transverse sectional view along a line of XIX-XIX in FIG. 19A.

In this example, a first grasping member 161 is a member having a rectangular cross section, and has a row of sawtooth-like teeth 162 on its grasping surface. A groove 163 is formed at the center of the cross section of the first grasping member 161 and extends in its axial direction. A first electrode 164 is buried in the groove 163. A pad member 165 is provided on the grasping surface of the first grasping member 161.

A second grasping member 166 to grasp a living tissue in cooperation with the first grasping member 161 is configured by the ultrasonic vibrating portion 31 at the distal end portion of the round bar-shaped probe 29. A portion of the outer circumferential surface of the second grasping member 166, the portion facing the first grasping member 161, is configured as a grasping surface 167 at a point being in contact with the pad 165 of the first grasping member 161. The outer surface of the second grasping member 166, Both sides of the grasping surface 167 on the portion of the outer circumferential surface of the second grasping member 166, the portion facing the first grasping member 161, are configured as a pair of second arc-shaped electrodes 168 which face the first electrode 164.

When the first grasping member 161 is pivotally moved in a direction in which the first grasping member 161 comes close to the second grasping member 166 and grasps a living tissue in cooperation with the second grasping member 166, the row of teeth 162 on the grasping surface of the first grasping member 161 contacts the living tissue, the pad member 165 on the grasping surface of the first grasping member 161 partially contacts the grasping surface 167 of the second grasping member 166 and forms a cut-join face. The first electrode 164 of the first grasping member 161 faces the pair of second electrodes 168 of the second grasping member 166 and forms coagulate-join faces.

This invention is not limited to the embodiments described hereinbefore. This invention may be embodied in various forms by modifying various component members without departing from an aspect of the invention. Further, the various component members disclosed in the above described various embodiments may be properly combined with each other. For example, some component members may be deleted from all components members shown in each embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising:
a first grasping member;
a second grasping member which is configured to open and close to the first grasping member, and to enable grasping a living tissue between them;
a high-frequency operation unit which includes a first electrode provided in the first grasping member and a second electrode provided in the second grasping member, the first electrode and the second electrode facing each other to provide a high-frequency operation region between them, and the high-frequency operation region being configured to coagulate the living tissue grasped by the first and second grasping members when high frequency current is applied between the first and second electrodes; and
an ultrasonic operation unit which includes an ultrasonic vibrating portion provided in one of the first and second grasping members, formed integrally with one of the first and second electrodes by using the same material as that of one of the first and second electrodes, and connected to an ultrasonic transducer to generate ultrasonic vibration, and a pressing portion provided in the other of the first and second grasping members and facing the ultrasonic vibrating portion, the pressing portion providing an ultrasonic operation region configured to press the living tissue grasped by the first and second grasping members and to coagulate and cut the pressed living tissue when the ultrasonic vibration is transferred to the ultrasonic vibrating portion from the ultrasonic transducer,
wherein the high-frequency operation region configured to treat living tissue and provided between the first electrode and the second electrode, and the ultrasonic operation region configured to treat living tissue and provided between the pressing portion and the ultrasonic vibrating portion, are arranged, respectively between the first grasping member and the second grasping member, and the high frequency operation region is positioned at a position excluding the ultrasonic operation region.

2. The surgical instrument according to claim 1, wherein
each of the first grasping member and the second grasping member is long and narrow,
a part of the first grasping member which faces the second grasping member has a dimension in a cross direction crossing a longitudinal direction of the first grasping member,
a part of the second grasping member which faces the first grasping member has a dimension in a cross direction crossing a longitudinal direction of the second grasping member, and
the cross-direction dimension of the part of the second grasping member is equal to or smaller than the cross-directional dimension of the part of the first grasping member, and the second grasping member does not project from the first grasping member in the cross direction.

3. The surgical instrument according to claim 1, wherein
the ultrasonic vibrating portion has a grasping surface which cooperates with the pressing portion and configured to grasp the living tissue,
each of the pressing portion of the ultrasonic operation unit and the grasping surface of the ultrasonic vibrating portion is long and narrow,
a combination of a cross section of the pressing portion and a cross section of the grasping surface includes a combination of a depression and a projection, and
the living tissue grasped by the grasping surface and the pressing portion is bent to make a surface contact with the grasping surface.

4. The surgical instrument according to claim 3, wherein
each of the first grasping member and the second grasping member is long and narrow,
a part of the first grasping member which faces the second grasping member has a dimension in a cross direction crossing a longitudinal direction of the first grasping member,
a part of the second grasping member which faces the first grasping member has a dimension in a cross direction crossing a longitudinal direction of the second grasping member, and
the cross-directional dimension of the part of the second grasping member is equal to or smaller than the cross-directional dimension of the part of the first grasping member, and the second grasping member does not project from the first grasping member in the cross direction.

5. A surgical treatment device comprising:
an operating portion which has a fixed handle and a movable handle which is rotational relative to the fixed handle;
an elongated sheath which is connected to a distal end part of the operating portion;

a drive member which is inserted in the sheath and which is configured to transmit a movement of the movable handle to a distal end part of the sheath;

an ultrasonic probe which is electrically conductive, which is inserted in the sheath, and which is configured to transmit ultrasonic vibration;

a treatment portion which is provided to a distal end part of the ultrasonic probe, and which has a treatment surface configured for transmitting ultrasonic vibration and high-frequency current to a living tissue, the treatment surface having a first treatment area provided in a central part thereof and a second treatment area, adjoining to each of both sides of the first treatment area relative to a longitudinal axis of the device, and inclined to the first treatment area with a predetermined angle; and a grasping portion which is connected to a distal end part of the drive member which is configured to open and close relative to the treatment surface of the treatment portion, and which grasps the living tissue in cooperation with the treatment surface of the treatment portion, the grasping portion having an insulating pad member provided at a central part of an area thereof corresponding to the treatment surface of the treatment portion so as to be in contact with the first treatment area so as to cut the grasped living tissue with the ultrasonic vibration, and the grasping portion having a high-frequency electrode surface formed in each of both sides of the pad member, corresponding to the both sides of the first treatment area, so as to separate and move from the longitudinal axis of the device and to approach the treatment surface.

6. The surgical treatment device according to claim 5, wherein each of the grasping portion and the treatment portion is long and narrow, a part of the grasping portion which faces the treatment portion has a dimension in a cross direction crossing a longitudinal direction of the grasping portion, a part of the treatment portion which faces the grasping portion has a dimension in a cross direction crossing a longitudinal direction of the treatment portion, and the cross-directional dimension of the part of the treatment portion is equal to or smaller than the cross-directional dimension of the part of the grasping portion, and the treatment portion does not project from the grasping portion in the cross direction.

* * * * *